(12) United States Patent
Murdjeva et al.

(10) Patent No.: US 11,776,223 B2
(45) Date of Patent: Oct. 3, 2023

(54) INTERACTIVE SYSTEM AND METHOD OF USE

(71) Applicants: Yuliana Ivanova Murdjeva, Dobrich (BG); Nicoletta Atanasova Murdjeva, Dobrich (BG)

(72) Inventors: Yuliana Ivanova Murdjeva, Dobrich (BG); Nicoletta Atanasova Murdjeva, Dobrich (BG)

(*) Notice: Subject to any disclaimer, the term of this patent is extended or adjusted under 35 U.S.C. 154(b) by 158 days.

(21) Appl. No.: 17/604,700

(22) PCT Filed: Apr. 18, 2019

(86) PCT No.: PCT/EP2019/060205
§ 371 (c)(1),
(2) Date: Oct. 18, 2021

(87) PCT Pub. No.: WO2019/149968
PCT Pub. Date: Aug. 8, 2019

(65) Prior Publication Data
US 2022/0198767 A1 Jun. 23, 2022

(51) Int. Cl.
*G06T 19/00* (2011.01)
*G09B 5/02* (2006.01)
*G09B 5/06* (2006.01)

(52) U.S. Cl.
CPC .............. *G06T 19/006* (2013.01); *G09B 5/02* (2013.01); *G09B 5/065* (2013.01)

(58) Field of Classification Search
None
See application file for complete search history.

(56) References Cited

U.S. PATENT DOCUMENTS

| | | | |
|---|---|---|---|
| 9,808,709 B2* | 11/2017 | Cozad | A63F 13/79 |
| 2012/0194420 A1 | 8/2012 | Osterhout et al. | |
| 2014/0184496 A1* | 7/2014 | Gribetz | G06F 3/013 |
| | | | 345/156 |
| 2016/0082319 A1* | 3/2016 | Macri | G16H 20/70 |
| | | | 434/257 |
| 2017/0319123 A1* | 11/2017 | Voss | G06V 10/945 |

(Continued)

FOREIGN PATENT DOCUMENTS

| | | |
|---|---|---|
| EP | 3312824 A1 | 4/2018 |
| WO | 2018033857 A1 | 2/2018 |

OTHER PUBLICATIONS

Taking Autism to the Sky, INC., "Our 2018 Drone: Unboxing Video", 2018, URL: https://tatts.org/events/2018-2/ (Year: 2018).*

(Continued)

*Primary Examiner* — David H Chu
(74) *Attorney, Agent, or Firm* — CrossPond Law

(57) ABSTRACT

An interactive system and a method of use for treatment and training a person with ASD or a similar condition or problem including primary part of holograms and holographic assistant, and secondary part of a group of drones and a robot that involves the use of a pair of holograms that imitate and demonstrate the functions of the right hemisphere of the brain and the left hemisphere of the brain, the exchange of information between them through the communication between the two. The interactive system can be used in training humanoid robots.

15 Claims, 7 Drawing Sheets

(56) References Cited

U.S. PATENT DOCUMENTS

| | | |
|---|---|---|
| 2017/0365277 A1* | 12/2017 | Park .................... G10L 15/1815 |
| 2018/0015347 A1 | 1/2018 | Janssen |
| 2018/0188850 A1* | 7/2018 | Heath ................... G06F 3/0202 |
| 2018/0308473 A1* | 10/2018 | Scholar ................... A63F 13/00 |
| 2019/0188788 A1* | 6/2019 | Baker, IV ............. G06T 19/006 |
| 2019/0270026 A1* | 9/2019 | Kaewkamnerdpong ..................... B25J 11/0015 |
| 2021/0387346 A1* | 12/2021 | Gillett .................. B25J 19/0075 |

OTHER PUBLICATIONS

International Search Report, PCT/EP2019/060205.
Written Opinion, PCT/EP2019/060205.

\* cited by examiner

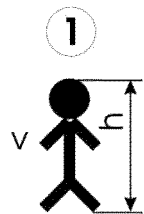 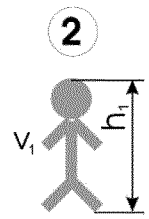 
Fig. 3a    Fig. 3b    Fig. 3c
Metric
| h, h, | k | h |
|---|---|---|
| 100 cm. | 1/7 | 14 cm. |
| 110 cm. | 1/8 | 14 cm. |
| 120 cm. | 1/9 | 13 cm. |
| 130 cm. | 1/9 | 14 cm. |
| 140 cm. | 1/10 | 14 cm. |
| 150 cm. | 1/11 | 14 cm. |
| 160 cm. | 1/11 | 15 cm. |
| 170 cm. | 1/11 | 15 cm. |
| 180 cm. | 1/12 | 15 cm. |
Fig. 3d

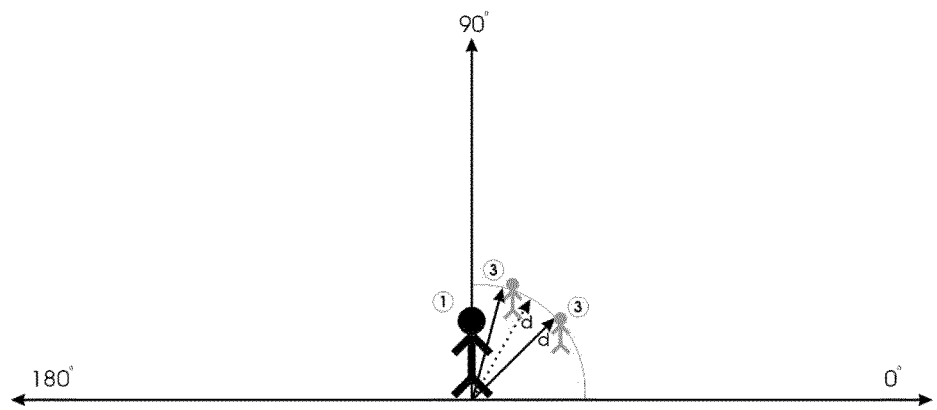
Fig. 4
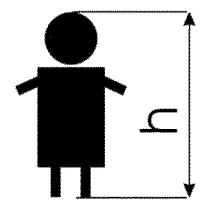
Fig. 5
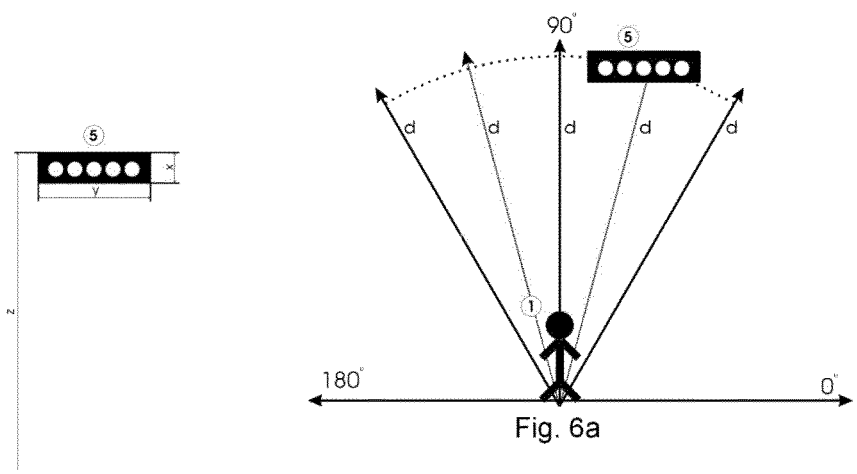
Fig. 6a
Fig. 6b

INTERACTIVE SYSTEM AND METHOD OF USE

The present application is in the field of treatment and training of people with autism spectrum disorders.

More specifically, the present invention relates to an interactive system comprising a hologram, a holographic assistant, a group of drones and a robot, and a method of use in treatment and training of people with autism spectrum disorders and similar conditions and problems.

The interactive system may be used for training for humanoid robots.

ASD is a lifelong developmental disability that affects how people perceive the world and interact with others. It affects more than 1 in 100 people and is commonly diagnosed in childhood, with boys being four times more likely to be diagnosed than girls. ASD is a spectrum condition, affecting people in different ways. Common characteristics are difficulties with social communication and interaction, and repetitive behaviour, routines and activities, to the extent that everyday functioning is limited and impaired. For example, people with ASD have difficulties with interpreting both verbal and non-verbal language, like gestures or tone of voice. Some may not speak or have limited speech capabilities. Some may prefer to use, or need to use, alternative means of communication, such as sign language or visual symbols. With regard to social interactions, there is often difficulty in recognising or understanding others' feelings and intentions, and in expressing their own emotions. People with ASD can therefore appear to be insensitive or be perceived as socially awkward and may find it hard to form friendships. The American Diagnostic and Statistical Manual (DSM) specifies three levels of severity in relation to social communication impairments and restricted, repetitive patterns of behaviour, namely: requiring support; requiring substantial support; requiring very substantial support.

People with ASD may also experience over- or under-sensitivity to sounds, touch, tastes, smells, light, colours, temperatures or pain. For example, they may find certain background sounds unbearably loud or distracting, and this can lead to anxiety or even physical pain.

ASD is not a disease and cannot be 'cured'. However, there is a variety of treatments, including different therapies, methods and activities designed to improve speech and behaviour, such as Floortime therapy; The "Blue Room" system; Method of Prof. Dr. Harry Schneider; Treatment Method of Roberto Morales; Autism treatment with Indian Ayurveda medicine—use of herbs; Chinese medicine—autism is treated with acupuncture with herbal supplements; Stem Cells as Autism Therapy; Dr. Stephen Edelson—Psychologist—the PECS—Alternate Card Communication System; Alternative therapies and activities—some of which are but not limited to: Music therapy, Biofeedback, Drum therapy, Ergo therapy, Hydro therapy, Art therapy, Hippo therapy, Kanis therapy, Feline therapy, Hyperbaric Oxygen therapy, Honey therapy, Sand therapy, Aromatherapy, activities in gardening, cooking, pastry.

Despite the wide range of existing exercises, therapies and methods used in combination or separately for the treatment of autism, there is no lasting result.

SUMMARY OF THE INVENTION

The present invention relates to an interactive system and method of use for treatment and training a person with ASD or a similar condition or problem, through the use of a pair of holograms that imitate and demonstrate the functions of the right hemisphere of the brain and the left hemisphere of the brain, the exchange of information between them through communication between the two.

References herein to 'ASD' mean not only ASD but related and/or similar conditions and problems.

The method employs an interactive system for a person with ASD (a participant), the interactive system comprising a number of interactive elements including a hologram, in a size ratio of approximately 1:1 with the participant;
a holographic assistant, duplicate, hologram, of a smaller size than the hologram;
a humanoid robot; and
a group of drones,
operated by computer specialists using a computer software management system and directed by a medical specialist.

The method further employs a therapy space for a person with ASD, wherein interactive elements as described above are arranged spatially in relation to the participant. This therapy space is safe for the participant.

Both the interactive system and the therapy space are aspects of the invention as described herein.

BRIEF DESCRIPTION OF THE DRAWINGS

FIG. 3 is representative of a participant, a hologram, and a holographic assistant that is proportional to the hologram.

FIG. 4 illustrates the positioning of the holographic assistant in relation to the participant, according to an embodiment of the invention.

FIG. 5 illustrates a robot in accordance with the present invention.

FIG. 6 illustrates a group of drones in accordance with the present invention and their positioning in relation to the participant.

DETAILED DESCRIPTION

Figure 1A:
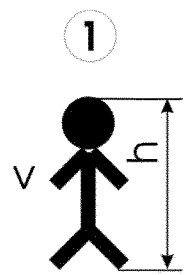
FIG. 1a illustrates a participant in the interactive system of the present invention.
Figure 1B:
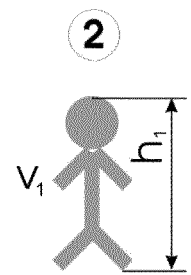
FIG. 1b illustrates a holographic representation (hologram) of the participant of FIG. 1a, in a scale of 1:1.

In one aspect, the present invention provides a method for training the brain of a participant, which method employs an interactive system comprising interactive elements including a hologram, in a size ratio of approximately 1:1 with the participant;
a holographic assistant, duplicate, hologram, of a smaller size than the hologram;
a humanoid robot; and
a group of drones,
operated by computer specialists using a computer software management system and directed by a medical specialist.

In the method of the present invention, the pair of holograms imitate and demonstrate the functions of the right hemisphere of the brain and the left hemisphere of the brain and the communication between the two.

The method of the present invention may employ a 'helping' hologram, as described in more detail herein.

In implementation of the method, a coach may be employed to assist a participant in his or her participation in tasks and activities delivered by the interactive system, as described in more detail herein.

By 'coach' a specialist with a professional qualification in the respective field of a given activity or therapy. For example, a hypo-therapy instructor is trained to work with horses and carry out the hypo-therapy activities for the particular participant. In addition to the professional qualification, he or she will generally have an additional qualification such as a psychotherapeutic and/or psychological qualification for working with a person with ASD.

By 'medical specialist' is meant psychiatrist (doctor of psychiatry). The psychiatrist can work either individually or in a team with other professionals, such as a psychologist, speech therapist or other specialists, depending on need and the condition of the participant.

The interactive system employed in the present invention also forms part of the present invention.

Thus, in another aspect, the present invention provides an interactive system for a participant, characterised in that the interactive system comprises interactive elements including
 a hologram, in a size ratio of approximately 1:1 with the participant;
 a holographic assistant, duplicate, hologram, of a smaller size than the hologram;
 a humanoid robot; and
 a group of drones.

As above, the interactive system is operated by computer specialists using a computer software management system and directed by a medical specialist, and a coach may be.

In a further aspect, the present invention provides a therapy space for a participant, characterised in that said therapy space contains interactive elements including
 a hologram, in a size ratio of approximately 1:1 with the participant;
 a holographic assistant, duplicate, hologram, of a smaller size than the hologram;
 a humanoid robot; and
 a group of drones,
each of said interactive elements being arranged spatially in relation to the participant.

In correspondence with the above, the actions and interactions of the interactive elements are operated by computer specialists using a computer software management system and directed by a medical specialist.

The following discussion applies to all aspects of the present invention and no statement is to be regarded as limiting of the invention.

People with ASD are very visual. They do not understand the meaning of the word "imagine" therefore there are two holograms that imitate the function of the human brain.

In some embodiments, the first hologram is adapted to stimulate the left hemisphere of the brain and the conscious. The first hologram may help a participant with self-acquaintance and self-acceptance and to self-like.

Thus, the hologram may be of approximately the same size as the participant and may be created in his or her image. The hologram may reflect the physical appearance of the user, and optionally also his or her characteristic speech, movement and behavioural traits. In this embodiment the hologram is a mirror image of the participant and in use of the system of the present invention, the participant will see him- or herself in the hologram and see that he or she can perform a given task, say given words, and make particular choices.

The hologram will generally be positioned to the left side of the participant and, depending on the participant's height, at a distance of 1.5 to 2.5 metres from the participant.

In some embodiments, the hologram is created with a different physical appearance to the user. For example, if the participant is seen to initially not like, or be uncomfortable with, a hologram in his or her own image, a hologram with a different physical appearance (an 'altered hologram') may be used initially, to be accepted.

The holographic assistant is a duplicate hologram and may also be referred to herein as a 'holographic assistant'. In some embodiments, the holographic assistant is adapted to imitate the function of right hemisphere of the brain and the subconscious. The holographic assistant is a connecting part of the hologram and the participant. Initially it displaced the participant to show him or her what to do. The holographic assistant may promote self-confidence and self-understanding in a participant, and faith in his or her capabilities.

Thus, the holographic assistant may be identical to the first hologram in every way apart from in size; it therefore also has the image of the user and reflects the physical appearance of the user, and optionally also his or her characteristic speech, movement and behavioural traits, but may be have a size ratio of, for example, 0.08-0.15:1 with the user.

The holographic assistant will generally be positioned to the right side of the participant and, depending on the participant's height, at a distance of 0.5 to 1.0 metre from the participant. It is deliberately smaller because the subconscious and the feelings cannot be seen.

In other embodiments, the holographic assistant may have an appearance different to that of the hologram. As above, this may be necessary when the participant is seen to not like, or be uncomfortable with, a hologram in his or her own image.

The relative sizes and positionings of the first hologram and assistant hologram with the participant reflect their respective roles in relation to the left hemisphere of the brain and logic (hologram) and right hemisphere of the brain and emotion (holographic assistant).

When either or both of the hologram and the holographic assistant does not have the image of the participant, it or they may be created, for example, as a cartoon character. When both the hologram and the holographic assistant are in the form of a cartoon character, they may be the same or different.

The robot is preferably emotion-sensitive. In some embodiments, the robot is toy-like. In some embodiments, the robot is from about 50 cm to about 100 cm in height, for example from about 55 cm to about 90 cm.

The robot may be positioned in front of the participant. The position of the robot is movable and not fixed, but generally the position of the robot should not be such that the ability of the participant to observe fully the hologram and the holographic assistant is impaired.

The group of drones comprises more than one drone and up to about 10 drones, although a greater number of drones may also be employed in the interactive system of the present invention. In some embodiments, the group of drones comprises 5, 7, or 9 drones.

The group of drones may be positioned, for example, in front of the participant; at a height of, for example, about 2.1 m to about 2.2 m from the ground; and positioned at a distance of, for example, from about 2 m to about 3 m from the participant.

The group of drones is used to attract the attention of a participant, distract the participant, and/or deliver prizes and other items to the participant. Each drone may be operated synchronized in group or independently.

Interaction between the elements in the interactive system may comprise:
Interaction of any two elements;
Interaction of any three elements; and
Interaction of all elements.

Which of the elements acts first in the methods of the present invention will depend on how the participant is seen to initially accept or choose the elements; thus, there is no fixed order for the action of the elements. The medical professional will direct which element starts in the method of the present invention, and how the method is continued, as described in more detail below.

The method of using the interactive system of the present invention for the treatment of ASD involves four steps:
(i) preparation of the interactive system;
(ii) initial preparation of the participant;
(iii) preparation of the participant for starting individual activities and therapies; and
(iv) preparation of the participant for group activities and therapies.

These steps are described in more detail below.

This interactive system can be applied in individual training of a participant; in preparation for any therapies, activities, methods, etc.; and can be applied in preparation of the participant for work in group. This interactive system can be applied in individual training of humanoid robots for individual developments without programming.

The therapy space of the present invention is physically separated from a control area which from which parents, carers, medical specialists and computer operators can observe the therapy space.

As described in more detail below, two computer specialists operate the interactive system described herein, under the direction of a medical specialist.

The specific arrangement of the interactive elements in relation to the participant is designed to engage both hemispheres of the brain and the conscious and subconscious mind in the person with ASD.

The principles behind the interactive system and therapy space of the present invention and methods for their implementation and use are described in the following paragraphs, with particular reference to the needs and characteristics of a person with ASD.

Mode of Action and Interaction within the System Between the Different Elements

The interactive system of the present invention may be regarded as including two sections containing the interactive elements; a 'primary' part, and a 'secondary' part.

The primary part comprises the hologram and the holographic assistant. Each is independently operated, such that they may work together, show different emotions, perform different actions, say different words, and apply different reasoning. In a therapeutic setting, the role of the hologram and holographic assistant is to show opposite opinion, reactions and to demonstrate different emotions. Through the actions and communication of the hologram and the holographic assistant the conscious and the subconscious are given a practical experience. Through the multiple repetitions and simulations of the actions and the communication of the hologram and the holographic assistant, the participant is taught and memories are created and recorded in his or her conscious and subconscious. Thus, they are optimally independently managed by different people, i.e., by different computer operators positioned in the control area.

The secondary part includes the robot and the group of drones. These elements are connected to, and managed and synchronised by, the hologram and the holographic assistant or by the computer specialists.

The two parts can work together and separately and interact with each other.

All of the elements, in both sections, can work independently with the participant.

Thus, in the primary section, the hologram and the holographic assistant are commanded separately, but synchronised and there is interaction between the two elements: hologram-holographic assistant and holographic assistant-hologram.

Either or both of the elements of the secondary part, i.e., the robot and/or the group of drones, may supplement the work of the primary part.

For example, there may be interaction between the either or both elements of the primary part and the robot; namely: hologram-robot, holographic assistant-robot, hologram-holographic assistant-robot, and robot-hologram, robot-holographic assistant, robot-hologram-holographic assistant.

Alternatively, or in addition, interaction between the either or both elements of the core section and the group of drones, namely: hologram-group of drones and holographic assistant-group of drones or hologram-holographic assistant, hologram-robot, hologram-group of drones, holographic assistant-hologram, holographic assistant-robot, holographic assistant-group of drones, hologram-holographic assistant-robot, robot-hologram, robot-holographic assistant, robot-hologram-holographic assistant, robot-group of drones.

Method of Use of Interactive System for Treatment and Training for People with ASD and Training of Humanoid Robots The method of using the interactive system of the present invention for the treatment and training of people with ASD and similar conditions and problems and the training of humanoid robots involves four steps:
(i) preparation of the interactive system;
(ii) initial preparation of the participant;
(iii) preparation of the participant for starting individual activities and therapies; and
(iv) preparation of the participant for group activities and therapies.

The interactive system can be used without age restrictions.

Preparation of the Interactive System

The hologram and holographic assistant are created, for example, with full visual identity to the participant. The size of the hologram may for example be in a ratio of 1:1 with the participant, and the size of the holographic assistant proportionally reduced.

Most preferably, the hologram and the holographic assistant are each the created not only with physical identity of the participant, but also to imitate his or her characteristic movements, mimics (i.e., facial features and expressions), behaviour, characteristic sounds, word combinations, and other characteristics. The hologram and the holographic assistant are each programmed to synchronise with each other, with the robot, and with the group of drones. Parents, carers, and medical specialists may all contribute to the preparation of the interactive system.

Initial Preparation of the Participant and Functions of the Interactive Elements In order to prepare the participant to use the interactive system of the present invention, the participant may be introduced into the therapy space, and on entry the participant sees all of the interactive elements. This will elicit a response from the participant, which will allow a medical specialist to make decisions, for example as to which interactive element will be preferred first in therapy. There is no fixed order, as the system of the present invention is designed to be personalised to each individual participant, and the starting element will be selected with the aim of relaxing the participant and encouraging him and her to sit within the therapy space.

The lack of physical presence of another person at the start will help the participant to relax and not to worry. In this way, the interactive system begins to do its job by bringing the participant unconsciously into a collective society. Once the participant is relaxed, the purpose is to start work with the hologram and the holographic assistant. Their different proportions, positioning and distance in relation to the participant will cause the participant to focus on each of the hologram and the holographic assistant separately, and in the full context of the therapy space.

Both brain hemispheres, and their live exchange of information, are imitated with the actions and communication of the hologram and the holographic assistant, associated also with consciousness and the subconscious. When communicating with the participant, the hologram and the holographic assistant behave in different ways, imitating both hemispheres of the brain.

An autistic person generally accepts everything literally. With the simultaneous action of the hologram and holographic assistant, he or she can be shown almost simultaneously two different variants and two different emotions. The actions of the conscious and the subconscious are shown in a given situation. Thus, the participant is given a choice, and in this way, may progress from passive mechanical repetition to becoming active. The availability of choice subtracts from a state of indifference in the participant, which state of indifference may reflect a neuronal deficiency. The actions and the communication of both the hologram and the holographic assistant may compensate for a compromised mechanism of mirror neurons in an autistic person. This helps for understanding the actions of other people.

The actions and communication of both the hologram and the holographic assistant a lively exchange of information between the two hemispheres of the brain, meaning the brain bridge is represented. The hologram and the holographic assistant normally display different opinions, feelings and states of mind (such a joy, happiness, sadness, etc.), they may behave differently and have different points of view. Dialogues between them reflect the inner dialogue that a person leads with him- or herself; for example, whether to do something or not; whether to buy something or not; whether to say something or not.

Through the actions and communication of the hologram and the holographic assistant, conscious and subconscious life experiences are given to the participant. The participant's thought and memories are created and recorded in his or her consciousness and subconscious. Thus, the hologram and the holographic assistant create the participant's faith in him- or herself and in his or her capabilities.

The hologram and the holographic assistant are programmed to work together, work alone, work sequentially, pause as if to think, concur or differ in emotion and opinion. When both holograms are interacting with each other and there is a lively exchange of information between them, but they cannot reach agreement on something, the robot may be employed. The robot represents an external opinion; an external decision; it will ask for explanations, as many times as necessary. When both holograms seek help from the robot, the participant should see that when he or she does not understand something or cannot do something on his or her own, he or she must seek out help. Help in this case is in the form of the robot. The participant may be involved and may participate in the choice to be made; however, if the participant does not participate, the holograms will make the choice with assistance from the robot.

Through repetition of the dialogue and actions between the hologram, the holographic assistant and the robot, the participant may be provoked to participate and make choices. For example, the robot may ask questions of the hologram and/or holographic assistant and try to involve the participant in the dialogue or help in decision making.

Thus, the robot will interact with each of the hologram and the holographic assistant individually until they reach a common solution. The robot creates the practice of repeating the action of the two holograms. It initiates the habit of repeating a certain situation, searching for opportunities, different options and solutions. It shows that there is no problem but different possibilities. Everything takes the form of play and entertainment, setting new goals and provoking desires. The purpose of the robot is to further affirm the belief of the participant in him- or herself and his or her capabilities.

The use of drones initially aims to attract the attention of the participant. With their appearance in a group, the drones interrupt and change the standard behaviour of the participant. He does not know how to react. In the process of interacting with the participant, the drones are used to provide support materials and reward to the participant. The reward is given for a repeated word, a given movement, a choice made for something the participant has done by himself. Awarding a reward is extremely important. It is reflected and remembered by the consciousness and the subconscious.

Use of the Interactive System in the Individual Training of Participants for Activities and Therapies After a participant is acquainted with the interactive system and therapy space of the present invention, a personalised programme of activity may be introduced. In this, a hologram will demonstrate an exercise, action or activity for the participant to perform, such exercise, action or activity having been designed for the participant by a supervisor. By dividing the hologram into separate holograms, the participant can be shown the whole process in detail. In this way, accumulation of the required skills and knowledge is smooth and gradual. Once the exercise, action or activity has been explained in detail and the whole helping hologram shown. For example, the holograms may demonstrate a flower to the participant. First the complete flower is shown, then it is divided into details and each detail is shown and explained until it is accepted by the participant. Then the whole flower is shown again. The supervisor is then introduced and explains an activity or exercise to the participant—the supervisor is introduced so that the participant can get acquainted with, and accept, this person. When the participant is seen to understand in detail the given exercise, action or activity and is comfortable with the supervisor, he or she can participate in the given exercise, action or activity, learning, repeating many times, and remembering it. In this way, he or she is fully assured of his or her ability to perform independently the given activity or therapy.

Use of the Interactive System for Preparation of the Participant for Group Activities and Therapies As a participant progresses with the interactive system of the present invention, he or she can move on from a single-participant therapy to one in which multiple participants are involved. Firstly, the participant will be presented with multiple holograms, for example, three, four, or more different holograms, each representing another user of the interactive system of the present invention. Thus, the participant may get acquainted with the idea of other participants, and observe them together, in a group. Once the participant is seen to be used to the multiple holograms, as well as knowing the supervisor and having performed independently and confidently in a given exercise, action or activity, he or she may be engaged in a real activity in a small group—firstly in a group that is familiar to him or her, and eventually, in a group in which none of the other participants is known to him or her. Thus, the interactive system of the present invention helps the participant to socialise and integrate.

Various embodiments of the invention are described in more detail below with reference to FIGS. 1-13. None of the following is intended to limit the invention in any way.

With reference to FIG. 1a, a participant (1) has a height h and a volume v. The participant (1) may be a person or a humanoid robot. The person can be from the autistic spectrum or other type of user. A hologram (2) (FIG. 1b) may have complete physical identity to the participant (1) in FIG. 1a. Physical identity is a set of features that allows for unambiguous identification of the participant, including at least some of height, build, body shape, length, color and shape of the hair, color and shape of the eye, shape and thickness of the eyebrows, shape of the nose, posture, gait and specific movements, for example.

Figure 2A:
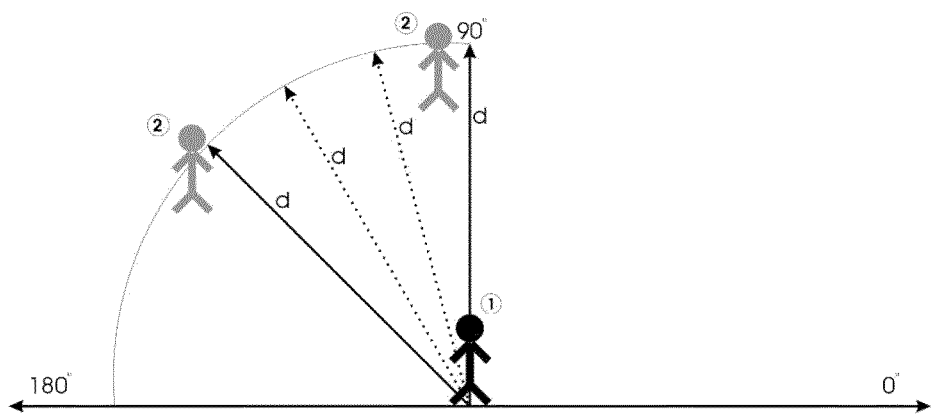
FIGS. 2a and 2b illustrate exemplary positions of the hologram in relation to the participant, according to an embodiment of the invention.
Figure 2B:
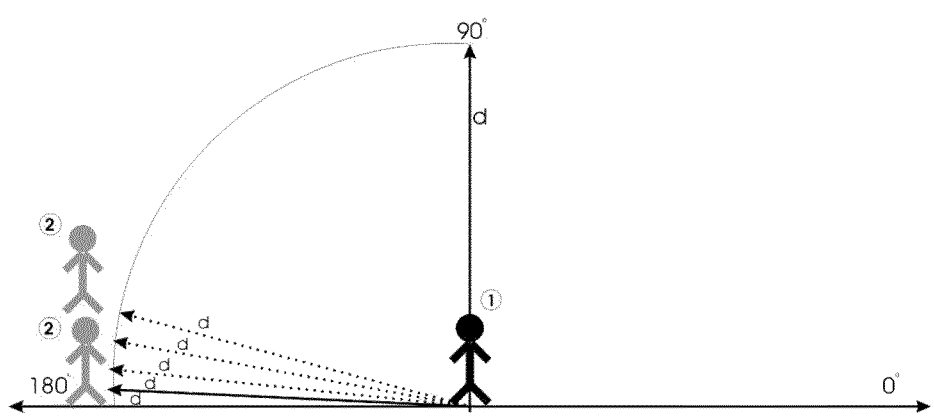

In some embodiments, in use, the hologram (2) is positioned on the left side of the participant (1), at a distance d from the participant, as illustrated in FIGS. 2a and 2b. Positioning is to the left side of the participant such that in use, the hologram is associated with the left hemisphere of the brain.

The positioning of the hologram in front of the participant, 'face-on', may be seen in more detail in FIG. 2a. Such positioning allows the participant to observe the mimics, gestures and movements performed by the hologram such that he or she may see them in detail, remember them and repeat them. The distance (d) of the hologram from the participant will depend on the height of the participant but may typically (but not exclusively) be from 1.0 to 2.5 meters. The distance d may be dependent on the height of the participant, such that for a shorter participant the hologram is closer to him or her, whereas for a taller participant the hologram is located farther away, such that it may be seen in its entirety. The hologram is located on the participant's left side and for optimal observation may be positioned at an angle of from 90 degrees to 150 degrees of an axis as shown by the double headed arrow in FIG. 2a, although greater angles are also possible.

FIG. 2b illustrates the positioning of the hologram next to the participant, sideways-on, to repeat a movement along with the participant, for example the right hand of the hologram with right hand of the participant. It is located on his left side and for better observation is positioned from 150 degrees to 180 degrees, but not limited to this. Depending on the height of the participant, the hologram is at a distance of 1 meter to 2.5 meters from him, for example, if it is shorter it is closer to him, if it is taller is located farther away, in order to be seen in its entirety, but is not limited to this.

The holographic assistant (3) is of smaller proportions than the participant (1) and the hologram (2), as illustrated in FIGS. 3a-3c, wherein h, $h_1$ and $h_2$ represent the height of the participant, hologram and holographic assistant, respectively, and v, $v_1$ and $v_2$ represent the volume or form of the participant, hologram and holographic assistant, respectively. Specific values are presented in FIG. 3d, in which the value k represents the coefficient of proportionality between the height of the participant and the hologram, and the holographic assistant.

As noted herein, the holographic assistant (3) may be a duplicate hologram having complete physical identity with the participant (1) and the hologram (2), but of different proportions. The holographic assistant (3) is deliberately made small, because it associates with the right hemisphere and the subconscious, and feelings and subconscious are not visible. Depending on the height of the participant, the holographic assistant may have a height (h) of 10 to 15 centimetres but is not limited thereto?

In some embodiments, in use, the holographic assistant (3) is positioned on the right side of the participant (1), at a distance d from the participant, as illustrated in FIG. 4. The holographic assistant (3) is positioned on the right side of the participant, because in use of the interactive system it is associated with the right hemisphere of the brain. It is positioned in front of the participant, 'face-on', such that the participant may observe the mimics, gestures and movements performed by the holographic assistant, seeing them in detail, remembering them and repeating them. The distance (d) of the holographic assistant from the participant will depend on the height of the participant. Since the holographic assistant is small, the distance (d) may typically be from 0.5 m to 1 m. For example, if the participant is shorter, the holographic assistant is closer to him or her and if the participant is taller, it is located further to be visible in its entirety. It is located on the participant's right side, and for better observation it is positioned from 30 degrees to 90 degrees but is not limited to this.

FIG. 5 depicts a humanoid robot (4) such as may be used in the interactive system of the present invention. In some embodiments, the humanoid robot resembles a toy, and in such case its height (h) is typically 55 to 90 cm, but not limited to this. Because the robot is movable, it does not have a strictly fixed position in the therapy space of the present invention; however its position will be such as not to obstruct the participant in observing the hologram and holographic assistant.

FIGS. 6a and 6b relate to the group of drones (5) and their positioning relative to a participant (1) in the therapy space. In some embodiments, there are 5, 7 or 9 individual droned (units) in the group of drones, but the number of units is not restricted to these numbers. The units are mini drones that are the same in size, shape and in functions they perform. They are managed remotely and may be used as a group or as independent units, depending on the task. FIG. 6a shows the positioning of the group of drones. They are located in front of the participant, typically at an angle of from 60 to 120 degrees along an axis as shown by the double headed arrow. The position of the group of drones is not limited to the illustrated positions and their position may change for example in order to react to change a given situation. In some embodiments, they are positioned at a distance (d) of 3-4 metres from the participant, but their position is not limited thereto. As illustrated in FIG. 6b, the drones are placed in a starting position on a fixed platform, for example having a width (x) of 60-70 cm and length (y) dependent on the number of drones but typically 3-4 metres; and being at a height (z) of typically 2.0-2.3 meters, so as to be out of the reach of the participant not to reach them. Values for x, y and z outside of the given ranges are also contemplated.

Figure 7:
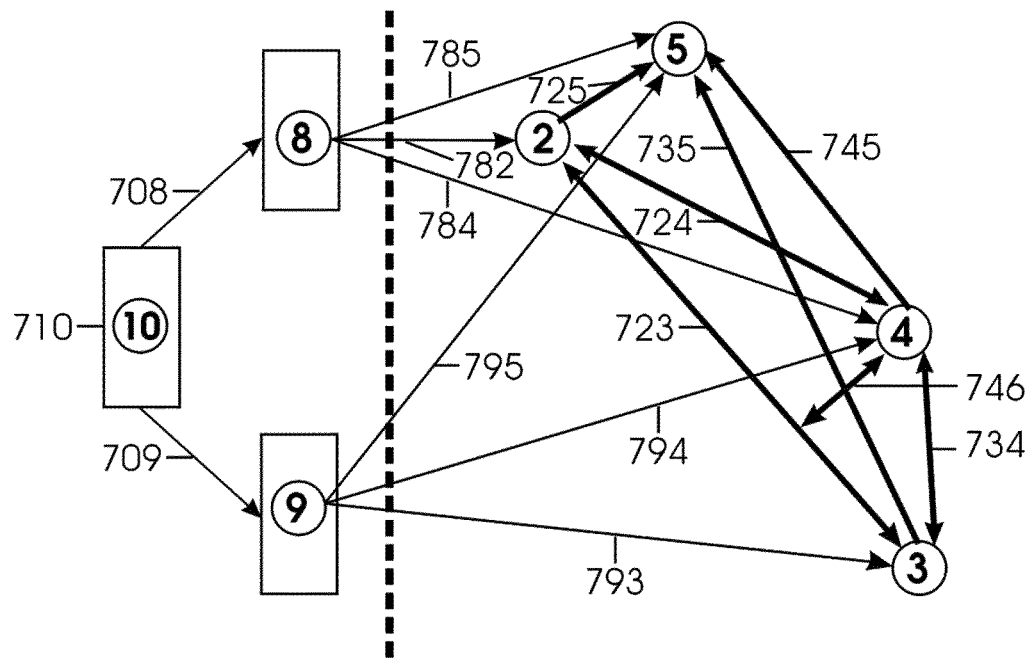
FIG. 7 illustrates an entire interactive system in accordance with the present invention; the relationships between the elements of the system; and the interaction between the main elements of the system.

FIG. 7 illustrates the entire interactive system, its management and interaction between the individual elements. The interactive system comprises of a primary part, namely a hologram (2) and a holographic assistant (3), and a secondary part, namely a robot (4) and a group of drones (5). It is managed by software that may be divided into two partitions in order to better manage the system. The management of the interactive system is performed from a distance and through a barrier, illustrated by the thick dashed line. A master computer (10) is equipped with software that is divided into two connections for ease of command, namely connection 708 to first computer specialist (8) and connection 709 to a second computer specialist (9). The first computer specialist (8) commands respectively a hologram (2) though a connection 782, a robot (4) through a connection 784 and a group of drones through a connection 785. A second computer specialist (9) commands a holographic assistant (3) through connection 793, robot (4) through a connection 794 and a group of drones (5) through a connection 795. The interaction and synchronization between separate elements of the interactive system is performed through the software and the work of the two computer specialists. The interaction between the elements of the interactive system can be in between two elements, all possible combinations, between three elements, all possible combinations and all elements together.

Connection 723 represents interaction between a hologram (2) and a holographic assistant (3), which interaction may include but is not limited to for example any of a monologue and action of each one of them, dialogue and action between the two, expressed in laughing, different sounds, speech, individual words, whole sentences, expressing the same opinion, expressing different opinions from one another, explaining, making different mimics, gestures, poses, showing and explaining of different emotional states, identical or different movements.

Connection 724 represents interaction between a hologram (2) and a robot (4), which interaction may include but is not limited to for example dialogue and action between the hologram and the robot, wherein the purpose is to obtain additional explanations and repetition by the hologram of an action, state or explanation. Connection 734 illustrates the interaction between a holographic assistant (3) and a robot (4), which interaction may include but is not limited to for example dialogue and action between the holographic assistant and the robot, wherein the purpose is to obtain additional explanations and repetitions by the holographic assistant of its different opinions, behaviours and actions of the hologram. Connection 725 represents an interaction between a hologram (2) and a group of drones (5) representing the control of the drones by the hologram, which interaction may include but is not limited to for example commands for giving helping materials and giving rewards to the participant. Connection 735 represents an interaction between a holographic assistant (3) and a group of drones (5) representing the control of the drones by the holographic assistant, which interaction may include but is not limited to for example commands for giving helping materials and giving rewards. Connection 745 represents an interaction between a robot (4) and a group of drones (5) representing the control of the drones by the robot, which interaction may include but is not limited to for example commands for giving helping materials and giving rewards. Connection 746 represents interaction between the robot (4) and the pair hologram (2) and the holographic assistant (3). In this connection, the hologram and the holographic assistant are accepted as a whole, that is, they act in a synchronized manner, come to a common opinion, to a common solution, and imitate common physical actions. The robot, talking to them, makes them repeat together the common decision or the common action. This interaction helps to repeat and confirm the commonly decided solution. Interactive system has interactions of three elements when more explanation, help, support and incentives are needed. The most commonly used three elements in combinations are a hologram (2), a holographic assistant (3) and a robot (4). The interaction may include but is not limited to for example monologues and actions of every one, and dialogue and action between the three. In this interaction, the differences between the hologram (2) and the holographic assistant (3) are clearly visible, as two different sides of a problem; two different ways behaviour. The robot focuses on differences, presents the problem as an opportunity, and offers new options for overcoming a given situation.

Different situations trough simulation that are being played show that there is always a way out and a solution to a problem, and the problem is presented as an opportunity. The other three elements that interact together, respectively, are a hologram (2), a holographic assistant (3) and a group of drones (5); a hologram (2), a robot (4) and a group of drones (5); and a holographic assistant (3), a robot (4) and a group of drones (5). In these triples the purpose is to use the group of drones (5) respectively by the hologram, holographic assistant or robot. The use of the group of drones (5) by one of the elements of the interactive system depends on the current situation, the needs of the participant and which of the three is the most appropriate one to command the group of drones in a situation. All elements of the interactive system—hologram (2), holographic assistant (3), group of drones (5) and robot (4) participate in the interaction of the quadruple. They are used together when completing an action or activity.

The advantages of the interactive system are the lack of a person, the type of self-learning and the heterogeneity of the group—a large hologram, a small hologram, a group of drones and a robot.

Figure 8:
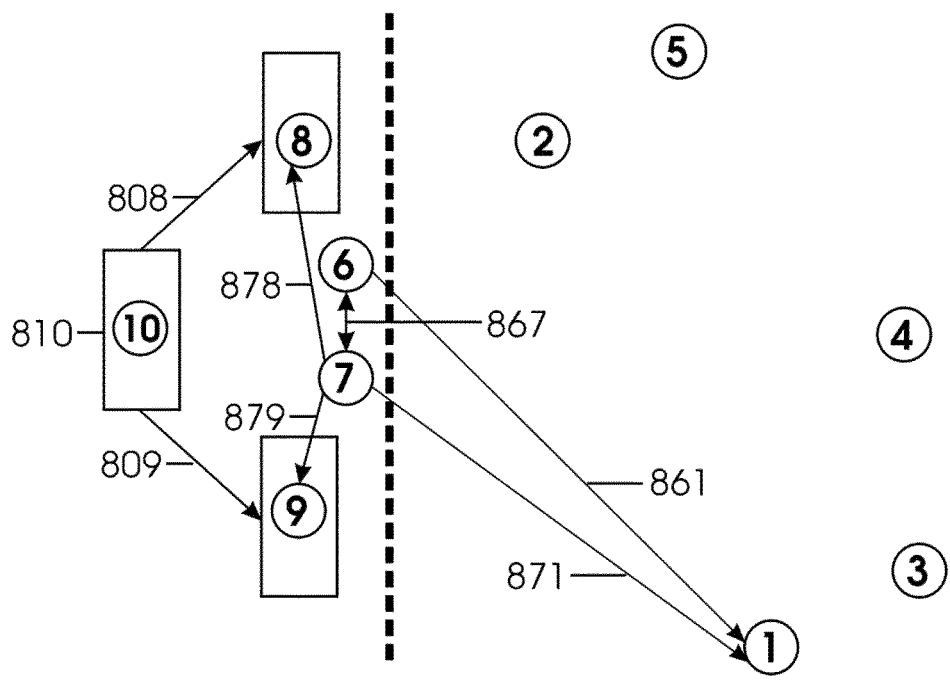
FIGS. 8-13 represent the interactive system in various modes of use, as described in more detail herein, illustrates a participant and the beginning action of an interactive system.

FIG. 8 illustrates the beginning of the work of the interactive system. The master computer (10) is equipped with software that for easier control is divided into two connections, namely 808 to a first computer specialist (8) and a connection 809 to a second computer specialist (9). All elements are positioned in the given room (therapy space), namely the hologram (2), holographic assistant (3), robot (4) and group of thrones (5). A barrier (dashed line), separates two areas such that the participant cannot see what is behind the barrier from the other side there is complete observation of the participant and interactive elements. Connection 861 represents the monitoring activity of a parent (6) to the primary response of a participant (1). Connection 871 represents the monitoring activity of a specialist (7) to the primary response of a participant (1). Connection 867 illustrates interaction between the parent (6) and specialist (7) representing information exchange, which helps the specialist (7) to decide with which computer specialist to start with in the delivery of therapy. Connection 878 represents a command by a specialist (7) to a first computer specialist (8) to initiate the interactive system by a hologram (2), a robot (4) or a group of drones (5). Connection 879 depicts a command by a specialist (7) to a second computer specialist (9) to initiate the interactive system by a holographic assistant (3), a robot (4) or a group of drones (5).

Figure 9:
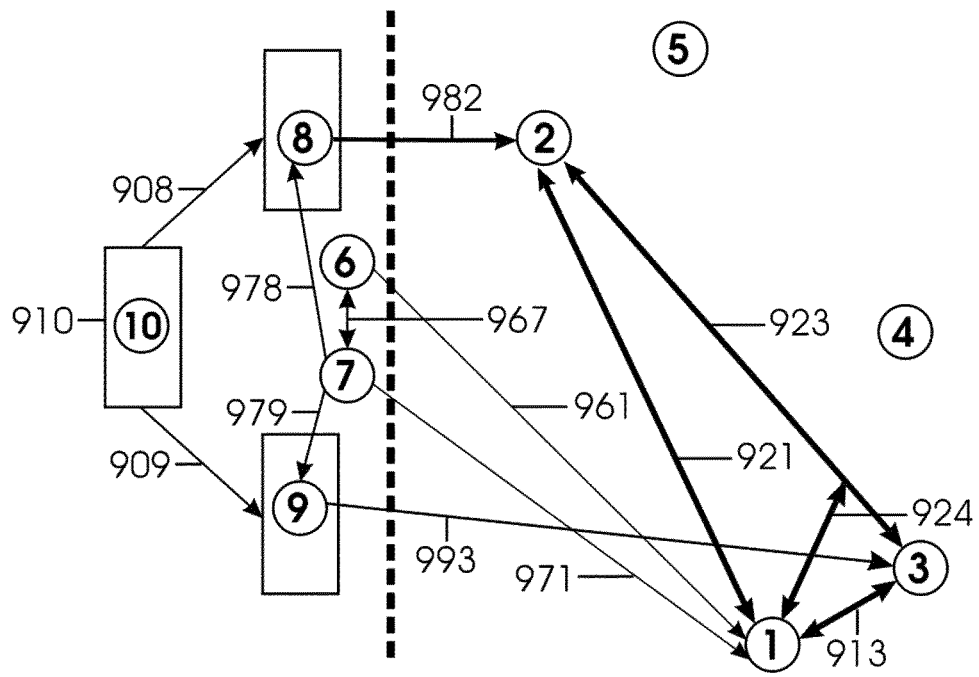

FIG. 9 illustrates one embodiment of an interaction of the primary part of the interactive system, namely a hologram (2), a holographic assistant (3) with a participant (1). FIG. 9 shows the beginning of individual preparation of a participant (1). In the individual preparation, the foundation of development is laid. Without it, there will be no lasting results in subsequent activities and therapies. The use of the interactive system begins with the observation shown by connection 961 of parent (6) to participant (1) and observation shown by connection 971 of specialist (7) to participant (1). After consultation between a specialist (7) and a parent (6), in relation to the reaction and behavior of a participant (1), the specialist (7) takes the decision shown in connection 967. Based on this decision, a specialist (7) chooses a beginning of the action of the interactive system. There are two options. The first option is specialist (7) to give a command to the first computer specialist (8) shown by connection 978 and this computer specialist (8) to initiate the action of the hologram (2) through connection 982. The second option is specialist (7) to give a command to the second computer specialist (9) shown by connection 979 and this computer specialist (9) to initiate the action of the holographic assistant (3) through connection 993. Of all interactions in the interactive system, this between the hologram (2), the holographic assistant (3) and the participant (1) is the most important. Autism is a disorder of social development that affects the development of the brain. Therefore, it is working with the brain through the two holograms. The two holograms are associated with the left and right hemispheres of the brain, with the consciousness and subconscious of the participant. Both hemispheres perform equally important functions. Through the two holograms and the interaction between them, the brain and the brain activity are visualized in a figurative sense. Numerous simulations are created, demonstrating, for example but not exclusively, the realization of mimics, gestures, sentences, movements, and way of behaviour, explanations, and actions. Connection 921 represents interaction of the hologram (2) with the participant (1). The purpose is for the participant (1) to get to know and accept himself as he is. Hologram (2) is associated with the functions of the left hemisphere. Connection 913 represents interaction of a holographic assistant (3) with a participant (1). The purpose is for the participant to see himself in small size, to become acquainted with his little self. The holographic assistant deliberately is small in size and closer to the participant because it associates with the right hemisphere and the subconscious, and feelings and subconscious are not visible. The left and right hemispheres of a person generally capture the uniformity and ambiguity of reality. Connection 923 shows interaction between a hologram (2) and a holographic assistant (3). This relationship is a bridge, the exchange of information between the left and right hemispheres. It has a key meaning for understanding an object, action, movement, but is not limited to that. Connection 924 represents an interaction between a hologram (2) along with a holographic assistant (3) and a participant (1). Together the two connections, 923 and 924, have a crucial meaning for the training and development of participant (1). An example chronology is: the participant sees an action played by the two holograms, it is explained in details to him by the holograms, understands the action, overcomes the fear, repeats the action, gets confidence in himself, memorizes the action, creates a positive emotion of success, creates and writes memories as a result of sensory experience or the communication process. The memory of the participant for the things he has experienced is as he has seen it. The example chronology is not limited to this sequence. Interactions are not limited to this sequence. The performance of interactions is determined depending on the condition and needs of the participant. An advantage when using the primary part of interactive system for interaction with the participant is a secure virtual environment for gaining real experience. Multiple virtual simulations lead to a change in thinking and feeling of the participant for himself or herself. When using the primary part, it starts to build and develop the habit of the participant to think positively. He is deliberately encouraged to have a positive emotional and mental perception of himself, people, and situations. Habits are created, that is, established way of behaviour.

This interactive system can train participants, users and humanoid robots. In connection with brain modeling of humanoid robots, the application of the interactive system will lead to better results in communicating with people.

Figure 10:
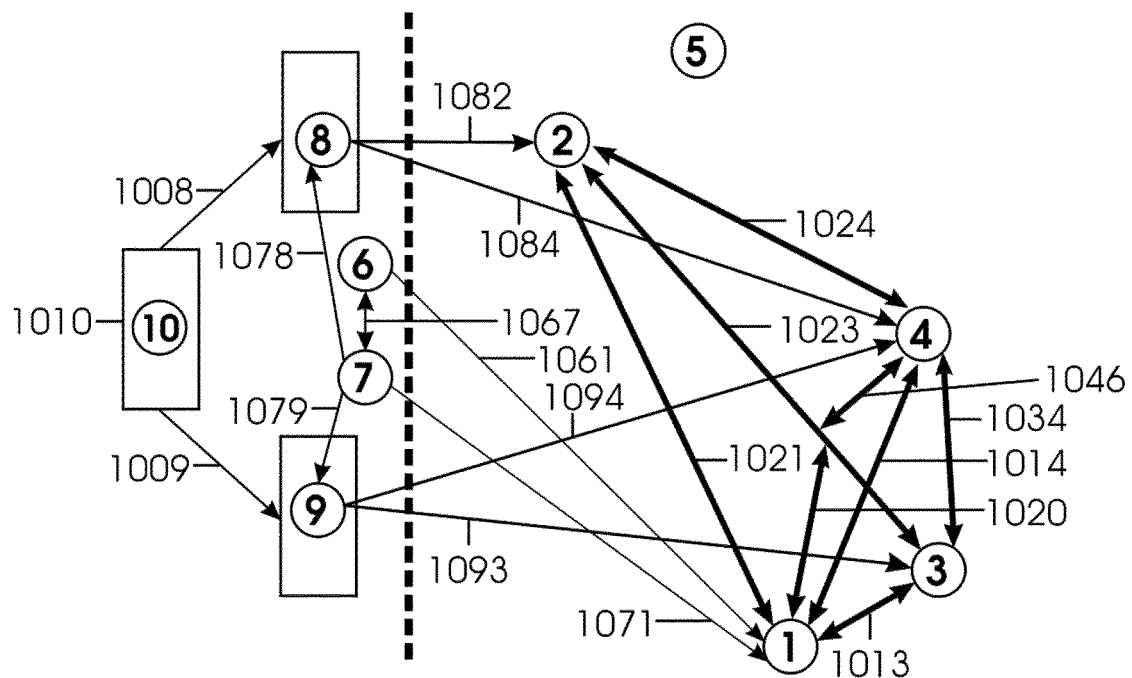

FIG. 10 illustrates one embodiment of the interactive system comprising three elements, respectively a robot (4), a hologram (2), a holographic assistant (3), a participant (1). The use of the interactive system begins with the observation represented by connection 1061 of parent (6) to participant (1) and observation represented by connection 1071 of specialist (7) to participant (1). After consultation between a specialist (7) and a parent (6), in relation to the reaction and behavior of a participant (1), the specialist (7) takes a decision, as represented by connection 1067. Based on this decision, a specialist (7) chooses an appropriate beginning of the action of the interactive system. There are two options. The first option is for a specialist (7) to give a command to the first computer specialist (8) as represented by connection 978 and for this computer specialist (8) to initiate the action of the hologram (2) through connection 1082 or to initiate the action of robot (4) through connection 1084. The second option is for the specialist (7) to give a command to the second computer specialist (9) as represented by connection 1079 and for this computer specialist (9) to initiate the action of the holographic assistant (3) through connection 1093 or to initiate the action of the robot (4) through connection 1094. Connection 1021 represents interaction of the hologram (2) with the participant (1). Connection 1013 represents interaction of a holographic assistant (3) with a participant (1). Connection 1023 represents the interaction between a hologram (2) and a holographic assistant (3). Connection 1020 represents an interaction between a hologram (2) along with a holographic assistant (3) and a participant (1). A robot is included in subsequent connections. It is the first element of the secondary part. It looks like a toy. As such it does not cause fear or anxiety in the participant. The robot performs the function of a little child who has not understood, always asks, wants something to be explained, is not sure, does not know, wants to get a new explanations and have things repeated. Through the robot (4), a participant (1) is shown that when something is not clear, an outside help should be sought, questions needs to be asked and explanations have to be asked for. The participant sees how this is achieved. Another function of a robot (4) is to reinforce, strengthen the action of the two holograms through new explanations and repetitions and to accentuate on the difference between them. Connection 1024 represents interaction between a hologram (2) and a robot (4). This connection aims to reinforce the action of a hologram (2), that is, the functions of the left hemisphere. Connection 1034 represents an interaction between a holographic assistant (3) and a robot (4). This connection aims to reinforce the action of a holographic assistant (3), that is, the functions of the right hemisphere. The robot (4) is in contact with a hologram (2) and a holographic assistant (3), and in each single situation an option of choice is offered as to which left or right hemisphere will dominate. Robot (4) offers options of choice, discussed them with participant (1), as shown in connection 1014 and subsequently makes the participant to choose. Thus, the participant is taken out of a passive state and becomes active. Connection 1046 represents the interaction between a hologram (2) and a hologram (3) and a robot (4). This connection serves as a repetition of common actions and common decisions, creating a habit, emotion and memory.

Figure 11:
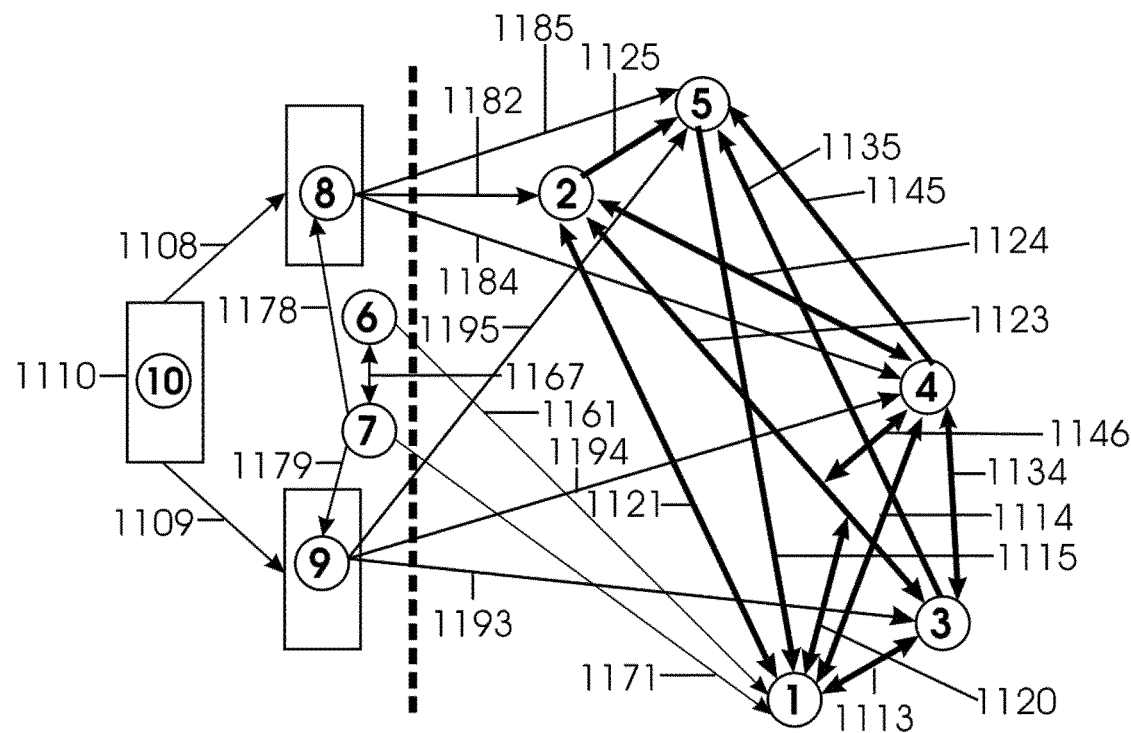

Interactions are not limited to the sequences described above. The performance of interactions is determined depending on the condition and needs of the participant. FIG. 11 illustrates one embodiment of the interactive system with four comprised elements, respectively a hologram (2), a holographic assistant (3), a robot (4), a group of drones (5) and a participant (1) in individual preparation. The group of drones consists of 5 or more drones that have the same size, shape and function. They are initially positioned on a stationary platform, in front of the participant, at a distance of 3 to 4 meters. A group of drones (5) is used in the individual preparation of a participant (1) in critical situation, giving helping materials and awarding prizes. For example, the group of drones (5) may be used if the participant (1) becomes irritated or angry, perhaps shouting, to shift his or her focus and to interrupt the direction of thinking. They are also used for example when the participant is distracted to help him or her to concentrate and to return him to the original task. In these two cases, the group of drones is commanded directly by a first computer specialist (8) through connection 1185 or by a second computer specialist (9) through connection 1195. Otherwise, the group of drones (5) is called by a hologram (2), a holographic assistant (3) or a robot (4). The use of the interactive system begins with the observation represented by connection 1161 of parent (6) to participant (1) and observation represented by connection 1171 of specialist (7) to participant (1). After consultation between a specialist (7) and a parent (6), in relation to the reaction and behavior of a participant (1), the specialist (7) takes the decision represented by connection 1167. Based on this decision, a specialist (7) chooses a beginning of the action of the interactive system. There are two options. The first option is for the specialist (7) to give a command to the first computer specialist (8), as represented by connection 1178 and for this computer specialist (8) to initiate the action of the hologram (2) through connection 1182 or to initiate the action of robot (4) through connection 1184. The second option is for the specialist (7) to give a command to the second computer specialist (9), as represented by connection 1179 and for this computer specialist (9) to initiate the action of the holographic assistant (3) through connection 1193 or to initiate the action of the robot (4) through connection 1194. Connection 1121 represents interaction of the hologram (2) with the participant (1). Connection 1113 represents interaction of a holographic assistant (3) with a participant (1). Connection 1023 represents the interaction between a hologram (2) and a holographic assistant (3). Connection 1120 represents an interaction between a hologram (2) along with a holographic assistant (3) and a participant (1). Connection 1024 represents interaction between a hologram (2) and a robot (4). Connection 1134 represents an interaction between a holographic assistant (3) and a robot (4). Connection 1146 represents the interaction between a hologram (2) with a holographic syringe (3) and a robot (4). Connection 1114 represents the interaction of a robot (4) with a participant (1). The following connections include the group of drones (5). It is the second element of the peripheral section. The group of drones are used as a group, but can also be used individually, depending on the task. Connection 1125 represents the interaction between a hologram (2) and a group of drones (5), which interaction may include but is not limited to the hologram controlling the group of drones, expressed in commands for giving helping materials and giving rewards. Connection 1135 represents the interaction between a holographic assistant (3) and a group of drones (5) representing the holographic assistant controlling the group of drones, which interaction may include but is not limited to commands for giving helping materials and giving rewards. Connection 1145 represents the interaction between a robot (4) and a group of drones (5) representing the robot controlling the group of drones, which interaction may include but is not limited commands for giving helping materials and giving rewards. Connection 1115 represents the group of drones (5) interacting with the participant (1).

Interactions are not limited to the sequences described above. The performance of interactions is determined depending on the condition and needs of the participant.

Figure 12:
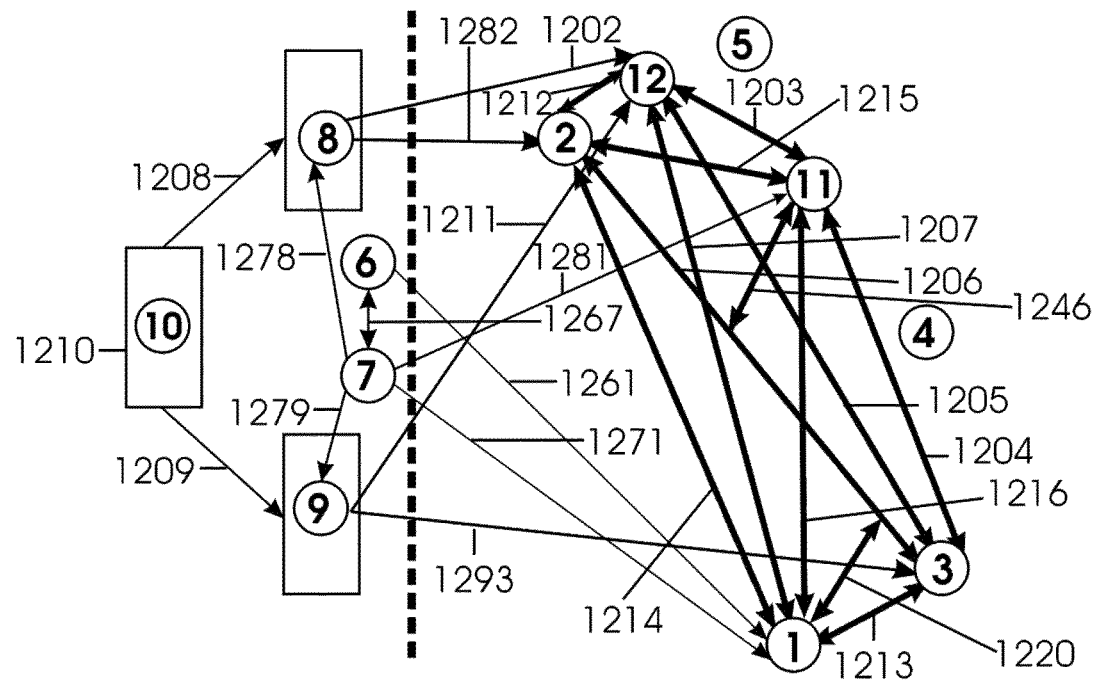

FIG. 12 illustrates one embodiment of the interactive system in the preparation of a participant (1) for activities and therapies, wherein a new element—a helping hologram (12) and the physical presence of a coach (11) are included to the interactive system. The elements of the interactive system are a hologram (2), a holographic assistant (3), a helping hologram (12) together with a trainer (11), and a participant (1). This preparation is necessary in order for the participant (1) to be familiar with the peculiarities and details of the corresponding activities and therapies and the coach who will lead them. Preparation helps a participant (1) easier and faster to accept the participation in his real life, overcoming the fear of the unknown, his insecurity, his ignorance. In the real activity, everything is familiar, everything is a repetition, as a participant (1) has participated in many virtual simulations. The beginning of the preparation starts with a helping hologram (12), which initially shows the whole activity statically. Then, one after another, pictures of the respective corresponding components of the activity or therapy are changed. They are discussed in turn by a hologram (2) and a holographic assistant (3) as a form, size, purpose, action, what association provoke, how it is performed, kind of complexity, explanations, but not limited to such. Following monologues and dialogues between a hologram (2) and a holographic assistant (3), they include a participant (1) in the discussion. A helping hologram (12) is commanded by a first computer specialist (8) through connection 1202 or by a second computer specialist (9) through connection 1211. It is positioned in front of a participant (1), but is not limited to, between a hologram (2) and a holographic assistant (3) but is not limited to, a distance of 1 to 2.5 meters but is not limited to this. The involvement of the coach is also important, as he is the first person to participate with the interactive system. Initially, he only communicated with a hologram (2) and a holographic assistant (3), and subsequently with a participant (1). The objective is that a participant (1) gradually becomes accustomed to his presence and accepts him as a participant and supervisor of the activity. Preliminary contacts with the coach help him in the real activity to accept him as something familiar. The coach (11) receives instructions from a specialist (7) through connection 1281. The use of the interactive system begins with the observation shown by connection 1261 of parent (6) to participant (1) and observation shown by connection 1271 of specialist (7) to participant (1). After consultation between a specialist (7) and a parent (6), in relation to the reaction and behavior of a participant (1), the specialist (7) takes the decision shown in connection 1267. Based on this decision, a specialist (7) chooses a beginning of the action of the interactive system. There are two options. The first option is specialist (7) to give a command to the first computer specialist (8) shown by connection 1278 and this computer specialist (8) to initiate the action of the hologram (2) through connection 1282. The second option is specialist (7) to give a command to the second computer specialist (9) shown by connection 1279 and this computer specialist (9) to initiate the action of the holographic assistant (3) through connection 1293. Interaction between a hologram (2) and a participant (1) is performed through connection 1214. Interaction between a holographic assistant (3) and a participant (1) is performed through connection 1213. Interaction between a hologram (2) and a holographic assistant (3) is performed through connection 1206. Interaction between a hologram (2), holographic assistant (3) and a participant (1) is performed through connection 1220. The connections with the helping hologram (12) are four. Interaction between a hologram (2) and a helping hologram (12) is performed through connection 1212. Interaction between a participant (1) and a helping hologram (12) is performed through connection 1207. Interaction between a holographic assistant (3) and a helping hologram (12) is performed through connection 1205. Interaction between a helping hologram (12) and a coach (11) is performed through connection 1203. The connections of the coach (11) are five. Interaction between a coach (11) and a hologram (2) is performed through connection 1215. Interaction between a coach (11) and a holographic assistant (3) is performed through connection 1204. Interaction between a coach (11) and a participant (1) is performed through connection 1216. Interaction between a coach (11) and a hologram (2) with holographic assistant (3) is performed through connection 1246.

Interactions are not limited to the sequences described above. The performance of interactions is determined depending on the condition and needs of the participant.

Figure 13:
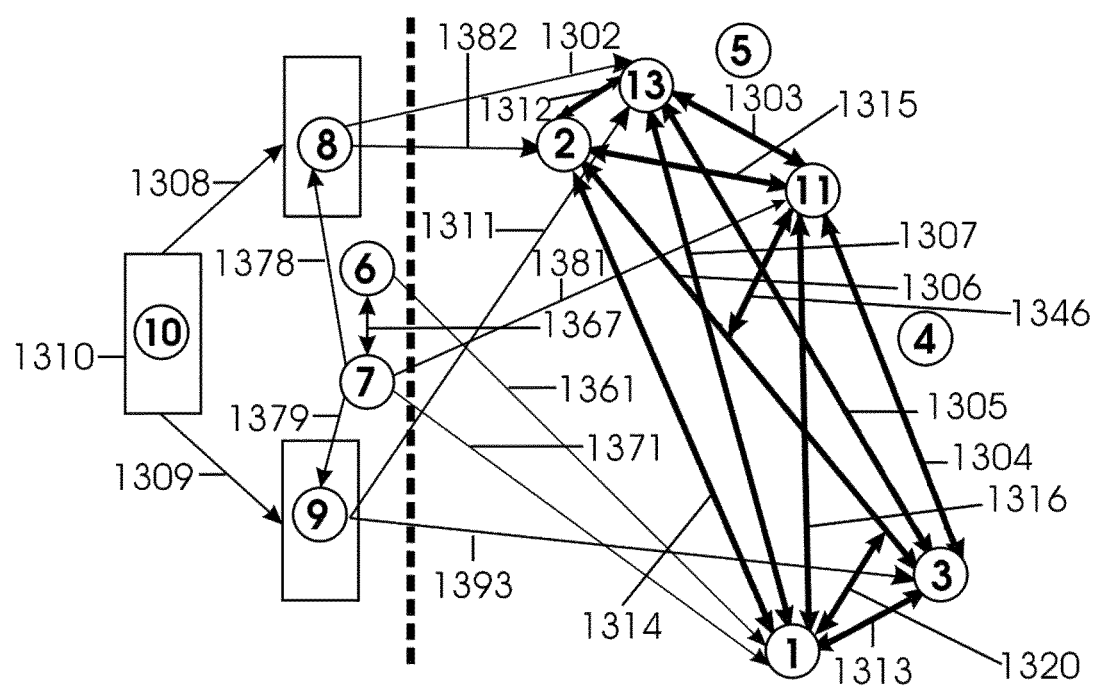

FIG. 13 illustrates one embodiment of the interactive system in the preparation of a participant (1) for group activities and therapies, wherein a new element—helping hologram (13) and the physical presence of a coach (11) are included to the interactive system. The elements of the interactive system are a hologram (2), a holographic assistant (3), a helping hologram (13) together with a trainer (11), and a participant (1). During preparation, attention is paid to a participant (1) that the work he has performed until than will be performed out in a group. A hologram (2) and a holographic assistant (3) explain what a group and a helping hologram (13) shows a static visual group of three participants, but it is not limited to. These are holograms of real participants who will actually be in group activities with a participant (1). Participant (1) meets each of the participants separately. The helping hologram (13) becomes a participant. The purpose is participant (1) to know in advance the other participants before the actual meeting. This makes it easier for him to contact, accept and communicate with new people. A helping hologram (13) is commanded by a first computer specialist (8) through connection 1302 or by a second computer specialist (9) through connection 1311. It is positioned in front of a participant (1), but is not limited to, between a hologram (2) and a holographic assistant (3) but is not limited to, a distance of 1 to 2.5 meters but is not limited to this. Initially, the coach (11) only communicated with a hologram (2) and a holographic assistant (3), and subsequently with a participant (1). The coach (11) receives instructions from a specialist (7) through connection 1381. The use of the interactive system begins with the observation shown by connection 1361 of parent (6) to participant (1) and observation shown by connection 1371 of specialist (7) to participant (1). After consultation between a specialist (7) and a parent (6), in relation to the reaction and behavior of a participant (1), the specialist (7) takes the decision shown in connection 1367. Based on this decision, a specialist (7) chooses a beginning of the action of the interactive system. There are two options. The first option is specialist (7) to give a command to the first computer specialist (8) shown by connection 1378 and this computer specialist (8) to initiate the action of the hologram (2) through connection 1382. The second option is specialist (7) to give a command to the second computer specialist (9) shown by connection 1379 and this computer specialist (9) to initiate the action of the holographic assistant (3) through connection 1393. Interaction between a hologram (2) and a participant (1) is performed through connection 1314. Interaction between a holographic assistant (3) and a participant (1) is performed through connection 1313. Interaction between a hologram (2) and a holographic assistant (3) is performed through connection 1306. Interaction between a hologram (2), holographic assistant (3) and a participant (1) is performed through connection 1320. The connections with the helping hologram (13) are four. Interaction between a hologram (2) and a helping hologram (13) is performed through connection 1312. Interaction between a participant (1) and a helping hologram (13) is performed through connection 1307. Interaction between a holographic assistant (3) and a helping hologram (13) is performed through connection 1305. Interaction between a helping hologram (13) and a coach (11) is performed through connection 1303. The connections of the coach (11) are five. Interaction between a coach (11) and a hologram (2) is performed through connection 1315. Interaction between a coach (11) and a holographic assistant (3) is performed through connection 1304. Interaction between a coach (11) and a participant (1) is performed through connection 1316. Interaction between a coach (11) and a hologram (2) with holographic assistant (3) is performed through connection 1346.

Interactions are not limited to the sequences described above. The performance of interactions is determined depending on the condition and needs of the participant.

Therapies that can be delivered by the present method and interactive system include, but are not limited to, Music therapy, Biofeedback, Drum therapy, Ergo therapy, Hydro therapy, Art therapy, Hippo therapy, Kanis therapy, Feline therapy, Hyperbaric Oxygen therapy, Honey therapy, Sand therapy, Aromatherapy, and activities in gardening, cooking, pastry.

The invention is further characterised with reference to the following claims.

The invention claimed is:

1. An interactive system for the treatment and training of a participant with autism spectrum disorder (ASD), characterised in that the interactive system includes interactive elements comprising:
   a hologram, in a size ratio of approximately 1:1 with a participant;
   a holographic assistant, duplicate the hologram, proportionally smaller than the hologram;
   a humanoid robot; and a group of drones;
and a software management system.

2. The interactive system of claim 1, wherein said first and second holograms are adapted to imitate and demonstrate the functions of the right hemisphere of the brain and the left hemisphere of the brain, the exchange of information between them through communication between the two.

3. The interactive system of claim 1, wherein the hologram is adapted to imitate the function of the left hemisphere of the brain and the conscious.

4. The interactive system of claim 1, wherein the hologram has the same physical characteristics, behaviour, specific gestures and movements, and speech characteristics as the participant.

5. The interactive system of claim 1, wherein said holographic assistant is adapted to imitate the function the right hemisphere of the brain and the subconscious.

6. The interactive system of claim 1, wherein the holographic assistant is substantially identical to the hologram in every way apart from in size.

7. The interactive system of claim 1, wherein the holographic assistant has a size ratio of 0.08-0.15:1 with the user.

8. The interactive system of claim 1, wherein the robot is an emotion-sensitive robot.

9. The interactive system of claim 1, wherein the group of drones comprises from 2 drones to about 10 drones.

10. The interactive system of claim 1, wherein each drone in the group of drones may be operated independently.

11. A method for use of interactive system for treatment and training of a participant with ASD, characterised in that said method comprises employing an interactive system comprising interactive elements including a hologram, in a size ratio of approximately 1:1 with the participant,
a holographic assistant, duplicate hologram, of a smaller size than the first hologram;
at least one helping hologram depending on the activity and/or therapy;
a humanoid robot; and
a group of drones; and
a software management system,
further comprising operating the interactive system with computer specialists under the direction of a medical specialist.

12. The method of claim 11, wherein said hologram and holographic assistant imitate and demonstrate the functions of the right hemisphere of the brain and the left hemisphere of the brain, the exchange of information between them through communication between the two.

13. The method of claim 11, wherein interaction between the elements in the interactive system comprises:
interaction between any two of said elements;
interaction between any three of said elements; and
interaction between all of said elements.

14. The method of claim 11, wherein there is no fixed order for the action of the elements, and the medical professional directs which element starts in said method.

15. The method of claim 11, comprising the steps of:
(i) preparing the interactive system;
(ii) performing initial preparation of the participant;
(iii) preparing the participant for starting individual activities and therapies; and
(iv) preparing the participant for group activities and therapies.

* * * * *